United States Patent
Bleuse et al.

[11] Patent Number: 5,904,900
[45] Date of Patent: May 18, 1999

[54] DEVICE FOR SAMPLING GASEOUS SUBSTANCES, LIQUIDS, AEROSOLS OR EVEN POWDERED MATERIALS FOR IN SITU ANALYSIS

[75] Inventors: Patrick Bleuse, Bois-d'Arcy; Pierre Clausin, Ville-d'Avray; Christian Heurtel, Vert-le-Petit, all of France

[73] Assignee: Etat Francais as represented by le Delegue General pour l'Armement, Paris, France

[21] Appl. No.: 08/945,482
[22] PCT Filed: Apr. 25, 1996
[86] PCT No.: PCT/FR96/00633
   § 371 Date: Nov. 28, 1997
   § 102(e) Date: Nov. 28, 1997
[87] PCT Pub. No.: WO96/34266
   PCT Pub. Date: Oct. 31, 1996

[30] Foreign Application Priority Data

Apr. 28, 1995 [FR] France .................................. 95 05320

[51] Int. Cl.⁶ .................. G01N 1/02; G01N 1/00
[52] U.S. Cl. .................. 422/99; 422/61; 422/83; 436/174; 436/181; 73/863.11; 73/863.12
[58] Field of Search .................. 73/863.11, 863.12; 436/174, 177, 181; 422/82.04, 83, 99, 88, 61

[56] References Cited

U.S. PATENT DOCUMENTS

| | | | |
|---|---|---|---|
| 4,542,641 | 9/1985 | Eyler | 73/26 |
| 4,565,786 | 1/1986 | Dunkhase et al. | 436/26 |
| 4,569,235 | 2/1986 | Conkle et al. | 73/863.03 |
| 4,924,714 | 5/1990 | Gross | 73/863.11 |
| 5,476,794 | 12/1995 | O'Brien et al. | 436/92 |
| 5,482,524 | 1/1996 | Nakano et al. | 55/267 |
| 5,500,369 | 3/1996 | Kiplinger | 435/309.1 |
| 5,595,709 | 1/1997 | Klemp | 422/88 |
| 5,665,314 | 9/1997 | Berger et al. | 422/89 |

FOREIGN PATENT DOCUMENTS

| | | |
|---|---|---|
| 2603698 | 3/1988 | France . |
| 2660873 | 10/1991 | France . |
| 3120362 | 12/1982 | Germany . |

*Primary Examiner*—Harold Y. Pyon
*Attorney, Agent, or Firm*—Oliff & Berridge, PLC

[57] ABSTRACT

The sampling device of the invention includes a collection unit with a collection surface (24), a sampling unit (30) engaging said collection surface (24), means for moving said sampling unit (30) and said surface relative to each other, heating means associated with the sampling means (30) for vaporising contaminant materials, and a suction nozzle (28) which connects to the inlet of an analyzing apparatus (1) and is designed to draw in the contaminant material vapours produced by the heating means. The invention is suitable for analyzing in situ gaseous substances, liquids, aerosols, and even pulverulent materials.

16 Claims, 2 Drawing Sheets

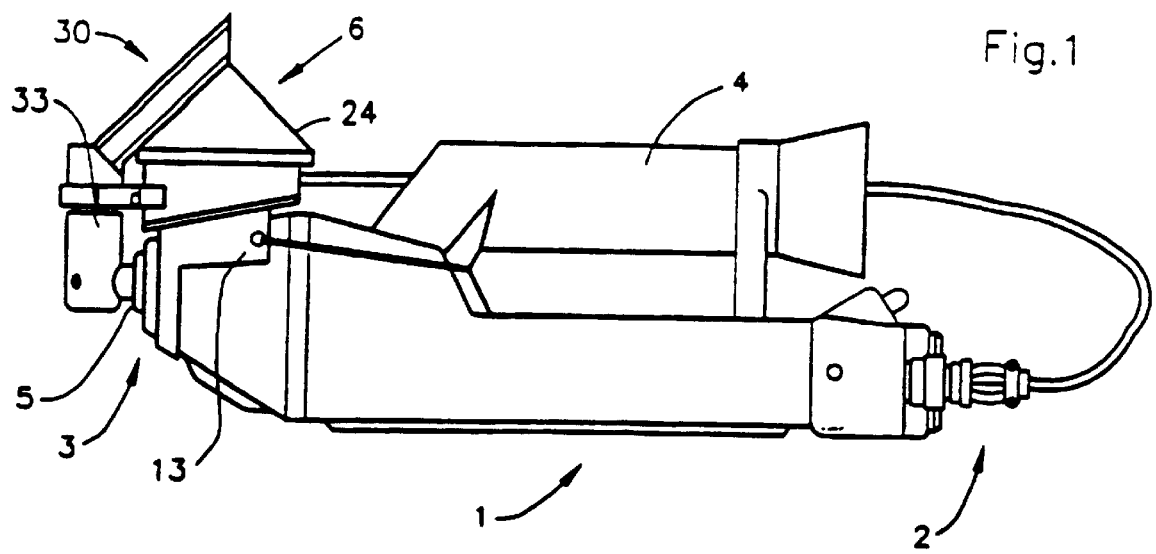
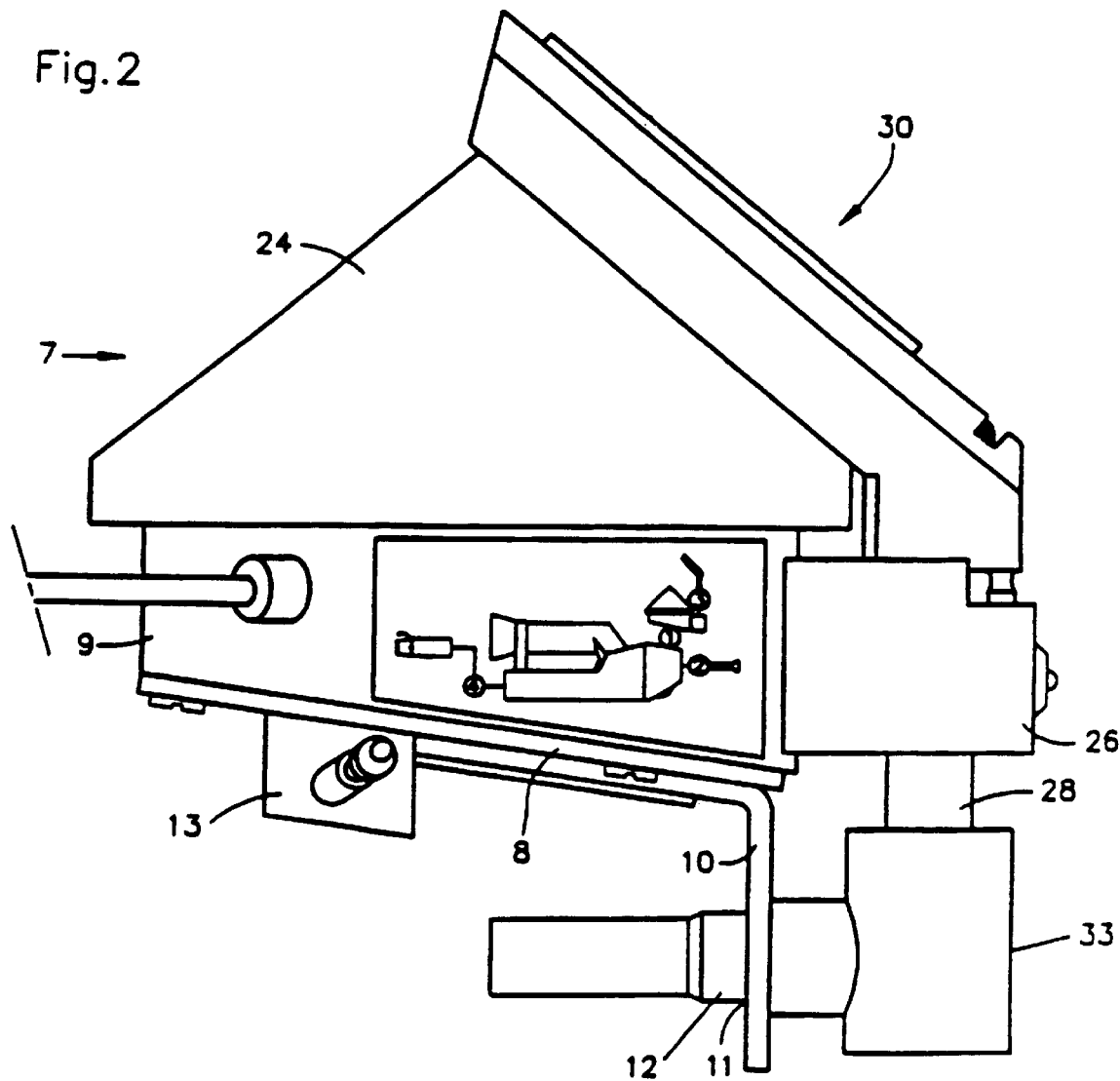

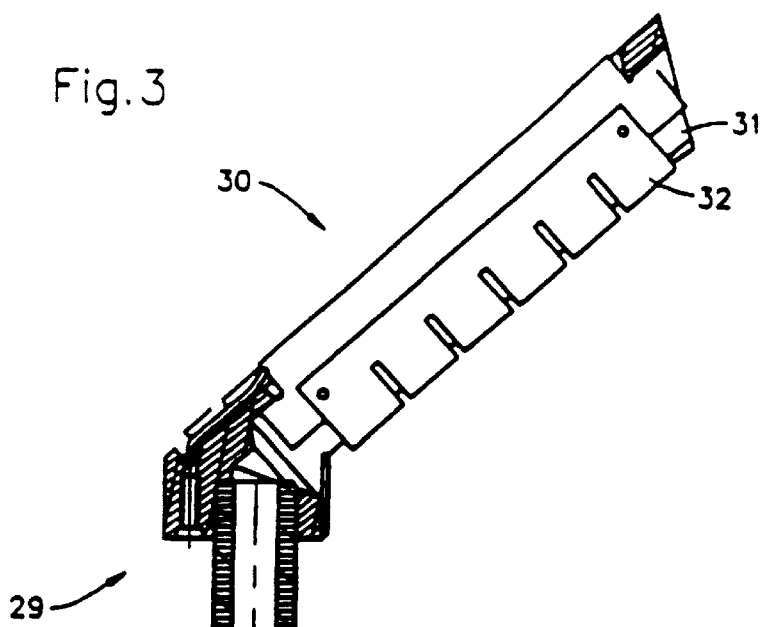
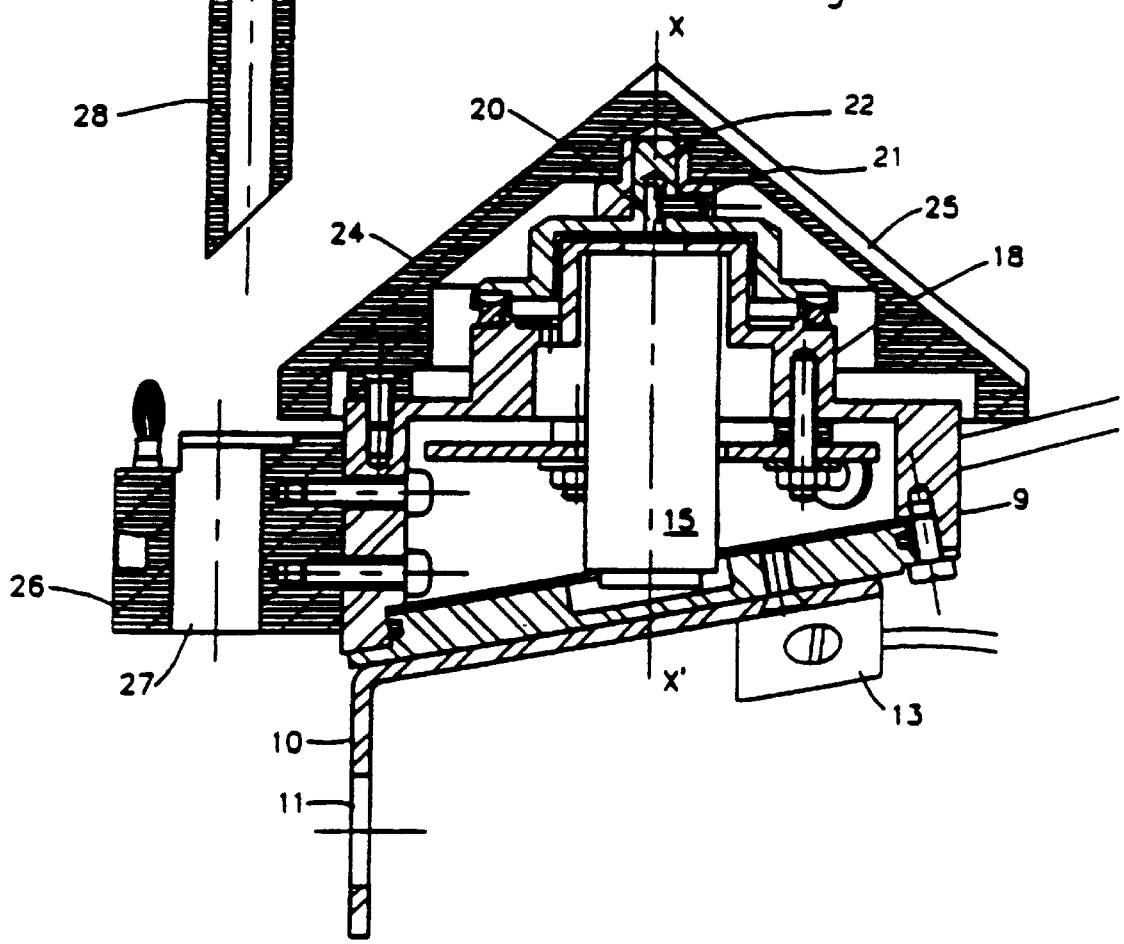

DEVICE FOR SAMPLING GASEOUS SUBSTANCES, LIQUIDS, AEROSOLS OR EVEN POWDERED MATERIALS FOR IN SITU ANALYSIS

This application is a 371 of PCT/FR96/00633 filed in Apr. 25, 1996.

BACKGROUND OF THE INVENTION

1. Field of the Invention

The present invention relates to a device for sampling gaseous substances, liquids, aerosols, or even powdered materials with a view to their analysis in situ in a device for analyzing gas composition.

It relates in particular, but not exclusively, to the detection of contamination by highly toxic substances, such as those used in chemical weapons, which can be spread in the form of gas, fine droplets, or even fine and widely spaced particles.

2. Description of Related Art

A portable gas-composition analyzer associated with a device for sampling and vaporizing the substance analyzed has already been proposed for such a detection purpose, notably by French patents 26 118 98 and 26 482 27 in the name of the Applicant.

According to French patent 2 648 227, the sampling device has a flexible tongue with an electrical heating resistor that vaporizes the substances collected by the tongue.

This device proves to require the intervention of an operator, who must collect the samples, then vaporize the liquids sampled so that the vapors produced are drawn into the analyzer as a gas whose composition is to be analyzed.

SUMMARY OF THE INVENTION

The particular goal of the invention is to achieve these results without the aid of any operator so that the sampler/analyzer assembly can be used as an autonomous sensor located at a site so that it can instantaneously detect the presence of atmospheric contamination or pollution.

To achieve this result, the sampler according to the invention comprises a collector having a collecting surface exposed to an atmosphere whose possible contamination is to be detected, a sampling element coming into contact with said collecting surface over an area thereof with reduced dimensions, means for effecting relative displacement between said sampling element and said surface so that said surface is swept by said sampling element in the course of at least one sweeping sequence, heating means associated with said sampling means for vaporizing any contaminants collected during the sweeping sequence, and an intake nozzle designed to connect to the inlet orifice of a gas-composition analyzer, said nozzle being designed so that it can draw in the contaminant vapors produced by the heating means.

Advantageously, said intake nozzle can include a shutter that allows either the intake of ambient air so that the gas composition of this air can be analyzed, or the intake of the vapors produced by the heating means to detect the presence of solid or liquid contaminants deposited on the collecting surface and collected by the collecting element.

Moreover, the sampler can include an automatic mechanism for actuating the heating means and analyzer at the end of the sweeping sequence.

BRIEF DESCRIPTION OF THE DRAWINGS

Embodiments of the invention will be described hereinbelow as nonlimiting examples with reference to the attached drawings wherein:

FIG. 1 is a side elevation of a gas-composition analyzer equipped with a sampler according to the invention;

FIG. 2 is an elevation of the sampler shown in FIG. 1;

FIG. 3 is a partial cross section of the sampling element and the intake nozzle of the sampler shown in FIG 1; and FIG. 4 is an axial section of the collector housing.

DETAILED DESCRIPTION OF PREFERRED EMBODIMENTS

In this example, the gas-composition analyzer consists of a portable, automatic device for flame spectrophotometry analysis of the type described in French patent 87 02 762 in the name of the Applicant.

The analyzer 1 has an elongate body having, on one side, electrical connecting means 2, and, on the other side, an intake head 3 to draw in the gases to be analyzed. It can be held by a handle 4 that contains a generator delivering hydrogen that participates in the combustion of the gas to be analyzed to produce the flame to be analyzed spectrographically.

The analyzer 1 includes a burner that has a window equipped with focusing optics on the axis of which is disposed a rotary chopper having a plurality of optical filters each of which corresponds to one element to be detected, and an optoelectronic cell placed at the focal point of the optics.

The electrical signal delivered by the optoelectronic cell is transmitted to an electronic processing circuit that determines and displays on a display the quantities of components detected in the gas. In the context of this application, the circuit has means for triggering an alert and possibly transmitting an alarm signal to a remote location when a target component has been detected.

The gas analyzed usually ambient air, is admitted into the burner through a turbine and an intake line communicating with the outside by an orifice 5 in intake head 3.

Movable sampler 6 associated with analyzer 1 is designed to be mounted on intake head 3 of the analyzer 1 by means of readily disconnectable assembly and fastening means.

The sampler 6 includes a collector housing 7 having a substantially frustroconical shape whose base 8, which contains cylindrical part 9, extends obliquely to general axis of symmetry XX'. The sampler 6 also has an assembly part 10 with a bend, one of the legs of said assembly part 10 having an opening 11 through which a tip 12 designed to fit into orifice 5 of intake head 3 passes, is attached to said base 8.

Collector housing 7 contains a coaxial electric motor 15 whose output shaft 20 passes through the small base constituting the vertex of the frustroconical part.

The motor 15 is supplied with electric power by analyzer 1 through a cable that connects to electrical connecting means 2.

Shaft 20, by means of a key 21, drives rotationally a drive part 22 with a substantially conical shape that extends parallel to and at a short distance from frustroconical part 18. The dynamic seal between these two parts is then provided by an O-ring 23 with an X-shaped cross section.

A coaxial collecting cap 24 can be disposed on drive part 22, the conical convex outer face of said coaxial connecting cap 24 constituting the collecting surface that will be exposed to the atmosphere whose contamination is to be measured.

In addition, this collecting cap 24 has a groove 25 along one of its generatrices, the role of said groove 25 being explained below.

A joining part 26 having a through hole 27 whose axis is parallel to axis XX' of the collector housing 7 and terminates in an area located opposite intake head 3 is screwed onto the cylindrical side face 9 of the collector housing 7 when sampler 6 is mounted on analyzer 1.

A tubular section 10, intake nozzle 28 of a collector/evaporator 29 of the type shown in FIG. 3 fits into the through hole 27.

Said collector/evaporator 29 has a sampling and heating arm 30 mounted at the upper end of tubular section 28 and has, inside a gutter-shaped support 31, a wiper 32 designed to abut the collecting surface of cap 24 over substantially the entire length of its generatrix.

For this purpose, gutter-shaped support 31 and wiper 32 are oriented such that, when section 28 has reached the bottom of through hole 27, gutter-shaped support 31 together with the collecting surface of cap 24 delimits a channel that communicates with the inside space of tubular section 28 and wiper 32 is applied to said collecting surface of cap 24 to retain any contaminants deposited thereon.

In this example, wiper 32 is in the shape of a flexible tongue that may be covered with an absorbing layer and has an electrical heating resistor. Electrical power is supplied to this resistor by the electrical power supply of analyzer 1 and is controlled by a switch when wiper 32 is opposite groove 25.

In addition, the lower end of sleeve 28 is sealably connected with intake head 5 of analyzer 1 by means of a T-shaped connector 33.

Thus, in an analysis phase, analyzer 1 takes in an air flow which passes successively from sampling and heating arm 30 to tubular section 28 to T-shaped connector 33.

The operation of the sampler described hereinabove comprises the following steps.

First of all, the assembly comprised of sampler 6 mounted on portable analyzer 1 is placed at the site to be monitored, with the axis of motor 15 and collecting cap 24 being oriented vertically. The convex side of collecting cap 24 points upward so that it is exposed to contamination by the target elements. This contamination can consist for example of a mist of fine droplets suspended in air. Operation of analyzer 1 triggers execution of a sequence of the following operating cycles.

Rotation of collecting cap 24 through one revolution so that groove 25 which initially was opposite sampling arm 30 returns to its initial position after rotating 360°.

A heating phase of wiper 32 to vaporize any polluting or toxic materials that have been deposited on the collecting surface and that have been collected by the wiper 32 during rotation of cap 24.

Simultaneously, with the heating phase, an analysis sequence during which analyzer 1 takes in gas from the atmosphere into sampling and heating arm 30 via a sleeve tubular section 28 and a T-shaped connector 33 and analyzes by spectrophotometry this gaseous atmosphere which may be laden with vapors of the contaminants or toxic materials collected.

If this analysis reveals the presence of a target element, analyzer 1 sends an alert signal, which may be a light and/or sound signal, and may send an alarm message by radio for example.

Of course, the operating cycles can follow each other continuously or discontinuously at preset intervals that could be adjustable.

It appears that the use of a conical cap 24 has the advantage of allowing water to flow in case of rain, as well as wind-borne solids that could affect the operation of analyzer 1.

Groove 25 provided in cap 24 has many advantages, such as preventing the heat in wiper 32 from damaging cap 24, channeling the flow of air drawn in by analyzer 1 to tubular section 28, eliminating the particles retained by wiper 32 when cap 24 rotates, and cleaning wiper 32 by action of its edge, which has a scraping effect on the part of wiper 32 exposed to dirt.

Advantageously, tubular sleeve 28 and/or connecting element 33 can be equipped with a shutter that can connect intake head 3 directly to the atmosphere without passing via arm 30 so that the phases in which the gas composition of the ambient air is analyzed and those in which the presence of liquid or solid contaminants suspended in the air is detected alternate.

The invention is not of course confined to the embodiment described hereinabove.

Thus, the collecting surface could have a shape different from that of a conical cap, it could for example be plain and have a continuous translational movement, similar to the winding of a film, or other alternating movement. It could also be cylindrical and be disposed coaxially to the intake head 3.

Likewise, wiper 32 could be designed to be selectively absorbent and hence concentrate the target substances. It could for example be coated with a silica gel deposited on the surface and held by silicone and be formed by juxtaposition of various tongue elements.

We claim:

1. A device for in situ sampling of contaminants including gaseous substances, aerosols, liquids or powdered materials in an atmosphere, the device connected to a gas-composition analyzer having an inlet orifice, the device comprising:
    a collector having a collecting surface that is exposed to the atmosphere, the collecting surface is rotatable;
    a sampling element for contacting the collecting surface;
    means for effecting relative displacement between the sampling element and the collecting surface so that the sampling element sweeps the collecting surface in the course of at least one sampling sequence to collect contaminants;
    heating means for vaporizing the contaminants collected during the at least one sweeping sequence thereby producing contaminant vapors; and
    an intake nozzle connectable to the inlet orifice of the analyzer such that the intake nozzle draws in the contaminant vapors.

2. The device according to claim 1, further including a shutter connecting the inlet orifice of the gas-composition analyzer either to the atmosphere or the intake nozzle.

3. The device according to claim 1, wherein said collector has a rotatable collecting cap and the collecting surface includes a conical convex face of the collecting cap.

4. The device according to claim 3, wherein said collecting surface has a groove extending along a generatrix of said collecting surface.

5. The device according to claim 1, wherein the sampling element includes a wiper that abuts the collecting surface, and the intake nozzle communicates with a gutter-shaped sampling arm that contains the wiper.

6. The device according to claim 5, wherein said wiper is a flexible tongue element and contains an electrical resistor.

7. The device according to claim 6, wherein said wiper contains ajuxtaposition of a plurality of flexible tongue elements.

8. The device according to claim 6, wherein said flexible tongue element is covered with an absorbing layer.

9. The device according to claim 8, wherein said wiper selectively absorbs contaminants.

10. A method for in situ sampling of gaseous substances, liquids, aerosols, or even powdered materials, using a gas-composition analyzer having an inlet orifice, the analyzer connected to a device having a frustroconical collector housing with a rotatable collector surface and a channel defining a groove, a sampling element having a wiper, an intake nozzle, an electric motor and heating means, the method comprising the steps of:

placing the analyzer at a site to be monitored;

positioning a convex side of said collector surface of said frustroconical collector housing upward such that said convex side of said collector surface is exposed to the atmosphere;

rotating said frustroconical housing using said motor;

collecting substances from the atmosphere deposited on said collector surface of said frustroconical collector housing using said sampling element;

directing the collected substances into said intake nozzle;

heating and vaporizing the collected substances; and analyzing the vaporized collected substances using the gas-composition analyzer.

11. The method according to claim 10, further comprising the step of transmitting a signal upon detection of predetermined substances in the analyzing substances.

12. The method according to claim 10, further comprising the step of rotating said frustroconical collector housing through a complete revolution of 360 degrees with respect to said sampling element.

13. The method according to claim 10, wherein the sampling element includes a wiper, the method comprising the further step of using said wiper to selectively absorb sampling substance deposited on the surface of said collecting surface.

14. The method of according to claim 10, wherein the inlet orifice of the gas-composition analyzer has a shutter, further comprising the step of selectively connecting the gas-composition analyzer to the atmosphere and said intake nozzle.

15. The method according to claim 10, further comprises the step using said groove for directing air to the gas-composition analyzer via said intake nozzle.

16. The method according to claim 15, further comprising the step of using said groove for eliminating particles retained by said sampling element during the rotation of said frustroconical collector housing.

* * * * *